United States Patent
Le Meur et al.

(10) Patent No.: US 11,925,500 B2
(45) Date of Patent: Mar. 12, 2024

(54) SYNCHRONISATION DEVICE AND METHOD FOR DETERMINING AN INSTANT OF THE RESPIRATORY CYCLE OF A PATIENT, AND ASSEMBLY COMPRISING A MEDICAL ROBOT

(71) Applicant: Quantum Surgical, Montpellier (FR)

(72) Inventors: Yann Le Meur, Versailles (FR); Lucien Blondel, Montpellier (FR); Fernand Badano, Lyons (FR); Bertin Nahum, Castelnau-le-Lez (FR)

(73) Assignee: Quantum Surgical, Montpellier (FR)

( * ) Notice: Subject to any disclaimer, the term of this patent is extended or adjusted under 35 U.S.C. 154(b) by 186 days.

(21) Appl. No.: 17/602,876

(22) PCT Filed: Apr. 8, 2020

(86) PCT No.: PCT/EP2020/060030
§ 371 (c)(1),
(2) Date: Oct. 11, 2021

(87) PCT Pub. No.: WO2020/208078
PCT Pub. Date: Oct. 15, 2020

(65) Prior Publication Data
US 2022/0160321 A1  May 26, 2022

(30) Foreign Application Priority Data
Apr. 12, 2019 (FR) ........................... 1903950

(51) Int. Cl.
*A61B 6/00* (2006.01)
*A61B 6/08* (2006.01)
(Continued)

(52) U.S. Cl.
CPC ............. *A61B 6/541* (2013.01); *A61B 6/08* (2013.01); *A61B 6/42* (2013.01); *A61B 6/4458* (2013.01); *A61B 6/461* (2013.01)

(58) Field of Classification Search
CPC ....... A61B 6/541; A61B 6/5264; A61B 6/461; A61B 6/445; A61B 6/42;
(Continued)

(56) References Cited

U.S. PATENT DOCUMENTS 6,501,981 B1 * 12/2002 Schweikard ........... A61B 6/527
378/69
2004/0254492 A1 * 12/2004 Zhang ................. A61N 5/1048
600/534
(Continued)

OTHER PUBLICATIONS

International Search Report dated Jul. 2, 2020 issued in PCT Application No. PCT/EP2020/060030.

*Primary Examiner* — Dani Fox
*Assistant Examiner* — Soorena Kefayati
(74) *Attorney, Agent, or Firm* — ARENTFOX SCHIFF LLP

(57) ABSTRACT

The disclosure is directed to a synchronization device and method for identifying a specific moment in a patient's respiratory cycle to aid medical interventions. The device includes a locating apparatus, a patient reference with radio-opaque markers, a detectable locating element, an X-ray detector, and a control unit for data recording and processing. The invention aims to improve the accuracy and efficiency of medical procedures by synchronizing them with the patient's respiratory cycle.

19 Claims, 4 Drawing Sheets

Figure 1:
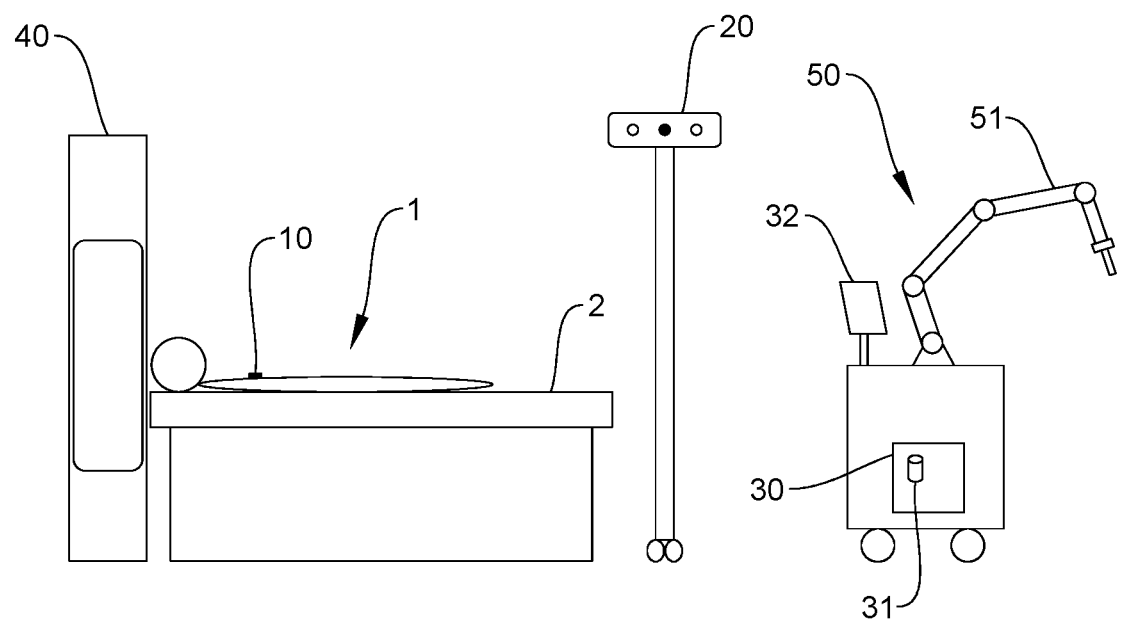

(58) Field of Classification Search
CPC .......... A61B 2017/00699; A61B 5/113; A61B 5/1135; A61B 2034/2055; A61B 2034/2051; A61B 6/08; A61B 6/4458
See application file for complete search history.

(56) References Cited

U.S. PATENT DOCUMENTS

| | | | |
|---|---|---|---|
| 2006/0025672 A1* | 2/2006 | Sendai | A61B 6/542 600/407 |
| 2008/0021300 A1* | 1/2008 | Allison | A61N 5/1031 378/65 |
| 2008/0177280 A1* | 7/2008 | Adler | A61B 90/10 901/41 |
| 2008/0208212 A1* | 8/2008 | Camus | A61B 34/70 901/14 |
| 2008/0267344 A1* | 10/2008 | Koehler | A61B 6/032 378/8 |
| 2009/0088622 A1* | 4/2009 | Mostafavi | A61B 5/1127 600/534 |
| 2009/0187112 A1* | 7/2009 | Meir | A61B 5/0077 600/595 |
| 2010/0063514 A1* | 3/2010 | Maschke | A61B 5/1135 606/130 |
| 2010/0067739 A1* | 3/2010 | Mostafavi | G06T 7/285 382/103 |
| 2011/0015521 A1* | 1/2011 | Faul | H04B 5/0062 250/492.1 |
| 2012/0039433 A1* | 2/2012 | Berkus | A61B 6/541 378/8 |
| 2012/0146796 A1* | 6/2012 | Margon | A61B 5/05 340/573.1 |
| 2012/0253217 A1* | 10/2012 | Mostafavi | A61B 5/0816 600/534 |
| 2012/0275657 A1* | 11/2012 | Kolthammer | A61B 6/037 382/107 |
| 2013/0303898 A1* | 11/2013 | Kinahan | A61B 6/032 600/407 |
| 2014/0072097 A1* | 3/2014 | Mukumoto | A61B 6/032 378/19 |
| 2014/0357988 A1* | 12/2014 | Grass | A61N 5/1067 600/1 |
| 2015/0131780 A1* | 5/2015 | Tsunoo | A61B 6/5235 378/62 |
| 2015/0139384 A1* | 5/2015 | Wu | A61B 6/541 378/8 |
| 2016/0220114 A1* | 8/2016 | Norita | A61B 5/0026 |
| 2017/0000380 A1* | 1/2017 | Gotman | A61B 5/062 |
| 2017/0014093 A1* | 1/2017 | Hosoki | A61B 6/5217 |
| 2017/0055910 A1* | 3/2017 | Kim | G06F 3/0445 |
| 2017/0281976 A1* | 10/2017 | Morf | A61B 5/7285 |
| 2017/0368369 A1* | 12/2017 | Heinrich | G06T 7/251 |
| 2018/0092698 A1* | 4/2018 | Chopra | A61B 90/39 |
| 2018/0140260 A1* | 5/2018 | Taguchi | A61B 6/032 |
| 2018/0221098 A1* | 8/2018 | Forsyth | A61B 90/11 |
| 2019/0038365 A1 | 2/2019 | Soper et al. | |
| 2019/0105514 A1* | 4/2019 | Amstutz | A61B 34/20 |
| 2019/0133499 A1* | 5/2019 | Auerbach | A61B 5/7282 |
| 2019/0183447 A1* | 6/2019 | Mori | A61B 6/463 |
| 2019/0298290 A1* | 10/2019 | Noji | A61B 6/488 |
| 2019/0374168 A1* | 12/2019 | Grodzki | A61B 5/7267 |
| 2020/0077962 A1* | 3/2020 | Kartäusch | A61B 5/7292 |

\* cited by examiner

SYNCHRONISATION DEVICE AND METHOD FOR DETERMINING AN INSTANT OF THE RESPIRATORY CYCLE OF A PATIENT, AND ASSEMBLY COMPRISING A MEDICAL ROBOT

CROSS-REFERENCE TO RELATED APPLICATIONS

This application is a National Phase of PCT/EP2020/060030, filed on Apr. 8, 2020, which claims priority to French Patent Application No. 1903950, filed on Apr. 12, 2019, the disclosures of which are hereby incorporated by reference in their entireties.

FIELD OF THE INVENTION

The present invention pertains to the field of minimally invasive medical interventions, in particular those guided by imaging. The present invention relates more particularly to a method for determining an instant of the respiratory cycle of a patient in order to assist a medical procedure.

PRIOR ART

Medical interventions (diagnostic, therapeutic and/or surgical) performed on a patient by a minimally invasive or percutaneous route are becoming more and more important, particularly in oncology in local cancer treatment, by acting directly on the cells of the affected organ, such as the liver, kidneys, lungs, pancreas, breast, prostate, etc.

These medical interventions generally require an operator to insert medical instruments inside the patient's body as far as a certain depth in order to reach a target anatomical zone that is to be treated.

In order to improve the precision of the medical insertion procedure, and also to limit the doses of radiation on the patient and the medical personnel, the operator can be assisted by a medical robot. The medical robot makes it possible for example, when associated with a control unit that plans the intervention on a medical image, to position an instrument guide according to the planning information. In this case, the instrument should preferably be inserted when the patient is in the same breathing conditions as he was in during the acquisition of the image that is used for the planning.

In order to perform the percutaneous intervention, an element called a "patient reference", comprising markers detectable in a medical image, is positioned beforehand on the patient's body, near the target anatomical zone. A medical image of the patient, provided with the patient reference, is acquired by an imaging device (for example a CT scan).

The medical intervention is planned using this intra-operative medical image. Alternatively, the medical intervention is planned using a pre-operative medical image, and the planning data are registered with the intra-operative medical image by realignment of images at the time of the intervention.

In general, it is considered that a given instant of the respiratory cycle of the patient corresponds to a given position of the target anatomical zone. During acquisition of the medical image, the patient is at a certain phase of the respiratory cycle. At the time of insertion of the instrument (subsequent to the image acquisition), it is necessary for the patient to be in the same phase of the respiratory cycle, so that the positions of the patient's organs correspond to the positions of these same organs during the acquisition of the medical image. If the insertion of the medical instrument is performed at a different phase of the respiratory cycle of the patient, the anatomy of interest may have shifted as a result of the respiration, and the target anatomical zone will therefore not be reached with precision.

The document EP 1 123 138 describes an imaging device coupled to a system delivering radiotherapy treatment according to the movements of a patient that are measured by a sensor and a camera. Radiotherapy treatment is delivered only when the movements of the patient do not exceed a certain threshold. However, it is necessary to image the patient at all times. The system is also very much dependent on the imaging device used.

The document U.S. Pat. No. 7,920,909 describes a method for determining a posteriori the time of the respiratory cycle at which a medical image is taken, by comparison with a series of medical images of the same patient that are taken at different times of the respiratory cycle of the patient. This method requires having a large number of medical images of the patient. Moreover, the exact instant of the respiratory cycle of the patient can only be determined with precision if a large number of medical images of the patient are available, so as to sample the respiratory cycle very finely. This method also implies that the respiratory cycle of the patient is regular.

The document WO 2019 026089 describes a belt surrounding the abdomen of a patient, the belt being provided with a first sensor indicating the size of the abdomen during the image acquisition, and a second sensor indicating the position of the patient during the image acquisition. These two sensors record the position of maximum inhalation of the patient when breathing. During the image acquisition and the medical intervention, the patient must block their breathing when this position of maximum inhalation is reached. This device does not give a precise indication as to the exact instant of the respiratory cycle during the acquisition of the medical image and is very much dependent on the patient. In addition, the respiratory cycle of the patient is considered regular.

DISCLOSURE OF THE INVENTION

The present invention aims to overcome all or some of the limitations of the solutions of the prior art, in particular those set out above.

To this end, the present invention proposes a synchronization device for determining an instant of the respiratory cycle of a patient in order to assist a medical intervention on said patient. This device comprises:
 a locating device,
 a patient reference, intended to be positioned on the body of the patient, and comprising radiopaque markers, at least one locating element configured to be detectable by the locating device, and an X-ray detector intended to cooperate with an X-ray imaging device,
 a control unit for recording the data from the locating device and the patient reference.

A synchronization device of this kind has the advantage of not being linked to any specific X-ray imaging device. Any type of existing X-ray imaging device can thus be associated with the synchronization device.

In particular embodiments, the locating device can also have one or more of the features described below, taken individually or in all technically feasible combinations.

In particular embodiments, the locating device is configured to continuously record movements of the patient reference, the movements of the patient reference corresponding to the respiratory cycle of the patient, and to transmit to the control unit. The control unit (30) is configured to:
- determine what is called a target position of the patient reference (10) in a medical image, acquired at a time when the patient's breathing has been blocked, from the at least one locating element (12), positioned on the patient reference (10), and the X-ray detector (13),
- determine what is called a candidate position of the patient reference (10), from the at least one locating element (12) positioned on the patient reference (10), at a time when the patient's breathing has again been blocked,
- compare the candidate position and the target position,
- when the candidate position is not within a predefined tolerance range with respect to the target position, to repeat the steps of determining the candidate position and of comparing the target and candidate positions until the candidate position is within a predefined tolerance range with respect to the target position.

Such a synchronization device advantageously permits the precise determination of the phase of the respiratory cycle during acquisition of the medical image, without considering that the respiratory cycle is regular.

Such a synchronization device also makes it possible to ensure the precision of the medical procedure insofar as the phase of the respiratory cycle of the patient is known with precision during the acquisition of the medical image and can be reproduced and controlled during the medical procedure.

In particular embodiments, the control unit is configured to determine, from all the positions taken by the patient reference during the period of the exposure to X-rays, the target position of the patient reference.

In a particular illustrative embodiment, the control unit is configured to determine the target position from the calculation of an average of all the positions taken by the patient reference during the period of the exposure to X-rays.

In another illustrative embodiment, the control unit is configured to determine the target position from the calculation of an average of all the positions taken by the patient reference during the period of the exposure to the X-rays, weighted by the X-ray dose received at each position.

In particular embodiments, the control unit is configured to estimate, from a predictive model of the respiratory cycle of the patient, the moment when the patient's breathing is blocked during the determination of a candidate position.

In particular embodiments, the control unit is configured to plan an intervention, assisted by a medical robot, between the steps of determining the target position and the candidate position.

In particular embodiments, the locating device is an optical locating device, and the patient reference has at least three optical locating elements.

In particular illustrative embodiments, the optical locating device is an infrared stereoscopic camera and the optical locating elements are reflecting spheres.

In particular embodiments, the locating device is an electromagnetic locating device, and the patient reference has at least one electromagnetic locating element.

In particular illustrative embodiments, the electromagnetic locating device is an electromagnetic field generator, and the at least one electromagnetic locating element has at least two conductive coils.

In particular embodiments, the X-ray detector is a dosimeter or a scintillator.

In particular embodiments, the synchronization device has a human-machine interface appliance configured to inform an operator, in the form of an acoustic signal and/or a visual signal, of the result of the comparison between the candidate position and the target position. The operator is then informed, depending on the signal received, whether or not the time is optimal to perform the desired medical procedure.

In particular illustrative embodiments, the human-machine interface appliance is a display screen.

The invention also relates to an assembly comprising a medical robot and the synchronization device according to at least one of its embodiments, the medical robot comprising a base, an articulated arm, of which one end is connected to the base, and a control unit. The medical robot advantageously makes it possible to perform the medical procedure in place of the operator.

In particular embodiments, the assembly can also have one or more of the features described below, taken individually or in all technically feasible combinations.

In particular illustrative embodiments, the control unit of the medical robot and the control unit of the synchronization device form one and the same control unit.

In particular illustrative embodiments, the medical robot has a human-machine interface appliance.

The invention also relates to a method for determining an instant of the respiratory cycle of a patient, in order to assist a planned medical intervention on said patient. The method according to the invention makes it possible, for example, to assist an operator in performing a medical procedure on the patient. The method comprises the steps of:
- 100—continuous recording of the movements of a patient reference placed near a target anatomical zone of the patient, the movements of the patient reference corresponding to the respiratory cycle of the patient,
- 101—acquisition, by an X-ray imaging device, of a medical image of said target anatomical zone of the patient,
- 102—determination of what is called a target position of the patient reference during the acquisition of the medical image, from at least one locating element, positioned on the patient reference, and an X-ray detector,
- 103—determination of a what is called a candidate position of the patient reference, from the at least one locating element positioned on the patient reference,
- 104—comparison of the candidate position and the target position.

The recordings of the movements of the patient reference in step 100 are carried out continuously, over time, throughout the duration of the method according to the invention.

The step 101 of acquisition of a medical image can be carried out while the patient's breathing is blocked. The blocking of the patient's breathing is temporary; the patient's breathing is unblocked once the medical image has been acquired.

Alternatively, this step 101 of acquisition of a medical image can be carried out without blocking the patient's breathing.

Such a medical image obtained during this step 101, on which the target anatomical zone to be treated is visible, is in particular intended to allow the operator to plan a medical procedure, performed by himself or by a medical robot assisting him for a medical intervention.

The target position of the patient reference is determined, during the acquisition of the medical image, from the movements of the at least one locating element configured to be detected by a locating device, and from the data obtained by the X-ray detector.

In an illustrative embodiment of the step 103 for determination of the candidate position, once the target position of the patient reference has been determined, and the planning of the medical procedure has been organized, the patient's breathing is again blocked. This blocking of the patient's breathing is temporary, being the time needed to determine what is called the candidate position of the patient reference, and to compare this candidate position with the target position of the patient reference, during this moment of blocking the breathing, in order to determine whether the patient's breathing has been blocked at the same phase of the respiratory cycle as during the acquisition of the medical image that has been used for the planning.

In another illustrative embodiment of the step 103 for determination of the candidate position, once the target position of the patient reference has been determined, and the planning of the medical procedure has been organized, the candidate position is determined without blocking the patient's breathing. The moment when the candidate position is close to the target position can for example be estimated from a predictive model of the respiratory cycle of the patient.

Whatever the illustrative embodiment of step 103, the medical procedure can be authorized and performed only when the patient is in the same breathing conditions.

Such a method makes it possible to determine the optimum moment when the operator can carry out the medical procedure. Such a method thus advantageously makes it possible to improve the precision of the medical insertion procedure, since the medical procedure is carried out when the breathing conditions of the patient are the same as those during the acquisition of the medical image that has been used for the planning.

The method according to the invention does not require as a prerequisite that the respiratory cycle is regular.

Such a method also advantageously makes it possible to limit the radiation doses to the patient and to the medical personnel, since the acquisition of a single medical image is sufficient to implement the method according to the invention.

The method according to the invention can also have one or more of the features described below, implemented individually or in each of their technically feasible combinations.

In particular embodiments, when the candidate position of the patient reference is not within a predefined tolerance range with respect to the target position, steps 103 and 104 are repeated until the candidate position of the patient reference is within a predefined tolerance range with respect to the target position.

Preferably, the tolerance range is ±10% of the target position.

In particular embodiments, the target position of the patient reference is determined from all the positions taken by the patient reference during the period of the exposure to X-rays, that is to say during the period of the acquisition of the medical image.

For example, the target position is determined by calculating an average of all the positions taken by the patient reference during the period of the exposure to X-rays.

In particular embodiments, the moment when the candidate position is within a predefined tolerance range with respect to the target position is estimated from a predictive model of the respiratory cycle of the patient.

In particular embodiments, in particular for anticipating the moment when the patient's breathing must be temporarily blocked in step 103, the moment when the patient's breathing is blocked is estimated from a predictive model of the respiratory cycle of the patient.

In particular embodiments, an acoustic signal and/or a visual signal is generated according to the result of the comparison between the candidate position and the target position of the patient reference. Such a signal advantageously makes it possible to alert the operator to whether or not he can perform the medical procedure.

In particular embodiments, the step of planning an intervention, in particular assisted by a medical robot, is carried out between step 102 of determining the target position and step 103 of determining the candidate position.

The invention also relates to a synchronization device for implementing said method according to at least one of its embodiments. The synchronization device comprises:
- a locating device, configured to continuously record movements of the patient reference, the movements of the patient reference corresponding to the respiratory cycle of the patient, and to transmit them to the control unit,
- a patient reference intended to be positioned on the patient's body and comprising radiopaque markers, at least one locating element configured to be detectable by the locating device, and an X-ray detector intended to cooperate with an X-ray imaging device (40),
- a control unit for recording the data from the locating device and the patient reference.

Such a synchronization device has the advantage of not being linked to any specific X-ray imaging device.

Such a synchronization device permits the precise determination of the phase of the respiratory cycle during the acquisition of the medical image, without considering that the respiratory cycle is regular.

Such a synchronization device also makes it possible to ensure the precision of the medical procedure insofar as the phase of the respiratory cycle of the patient is known with precision during the acquisition of the medical image and can be reproduced and controlled during the medical procedure.

In particular embodiments, the locating device can additionally have one or more of the features described below, taken individually or in all technically feasible combinations.

In particular embodiments, the control unit is configured to:
- determine the positions of the patient reference during the acquisition of the medical image, that is to say during the period of the exposure to X-rays, from the data of the at least one locating element positioned on the patient reference, and from the data of the X-ray detector,
- determine what is called a target position of the patient reference from all the positions of the patient reference during the acquisition of the medical image,
- determine what is called a candidate position of the patient reference from the at least one locating element positioned on the patient reference,
- compare the candidate position and the target position.

In particular embodiments, when the candidate position is not within a predefined tolerance range with respect to the target position, the control unit is configured to repeat the steps of determining the candidate position and comparing the target and candidate positions until the candidate position is within a predefined tolerance range with respect to the target position.

In particular embodiments, the control unit is configured to plan an intervention, assisted by a medical robot, between the steps of determining the target position and the candidate position.

In particular embodiments, the locating device is an optical locating device, and the patient reference comprises at least three optical locating elements.

In particular illustrative embodiments, the optical locating device is an infrared stereoscopic camera, and the optical locating elements are reflecting spheres.

In particular embodiments, the locating device is an electromagnetic locating device, and the patient reference has at least one electromagnetic locating element.

In particular illustrative embodiments, the electromagnetic locating device is an electromagnetic field generator, and the at least one electromagnetic locating element has at least two conductive coils.

In particular embodiments, the X-ray detector is a dosimeter or a scintillator.

In particular embodiments, the synchronization device has a human-machine interface appliance configured to inform an operator, in the form of an acoustic signal and/or a visual signal, of the result of the comparison between the candidate position and target position.

In particular illustrative embodiments, the human-machine interface appliance is a display screen.

The invention also relates to an assembly comprising a medical robot and a synchronization device according to at least one of the embodiments thereof and in accordance with the method according to at least one of the embodiments thereof, the medical robot having a base, an articulated arm, one end of which is connected to the base, and a control unit.

In particular embodiments, the assembly can additionally have one or more of the features described below, taken individually or in all technically feasible combinations.

In particular illustrative embodiments, the control unit of the medical robot and the control unit of the synchronization device form one and the same control unit.

In particular illustrative embodiments, the medical robot has a human-machine interface appliance.

PRESENTATION OF THE FIGURES

Figure 2:
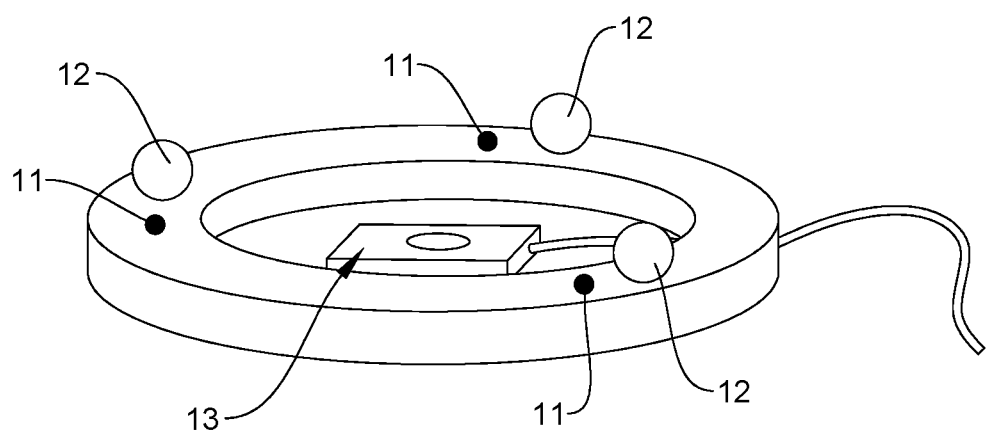
Figure 3:
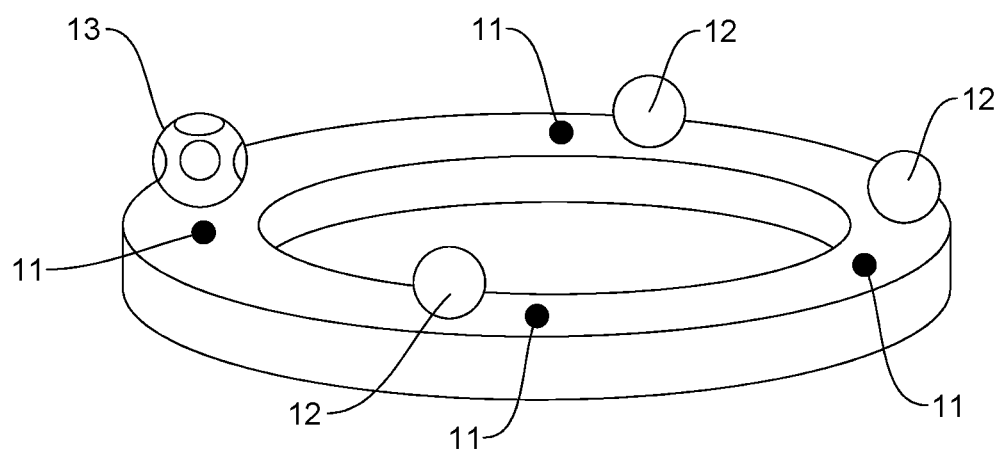
Figure 4:
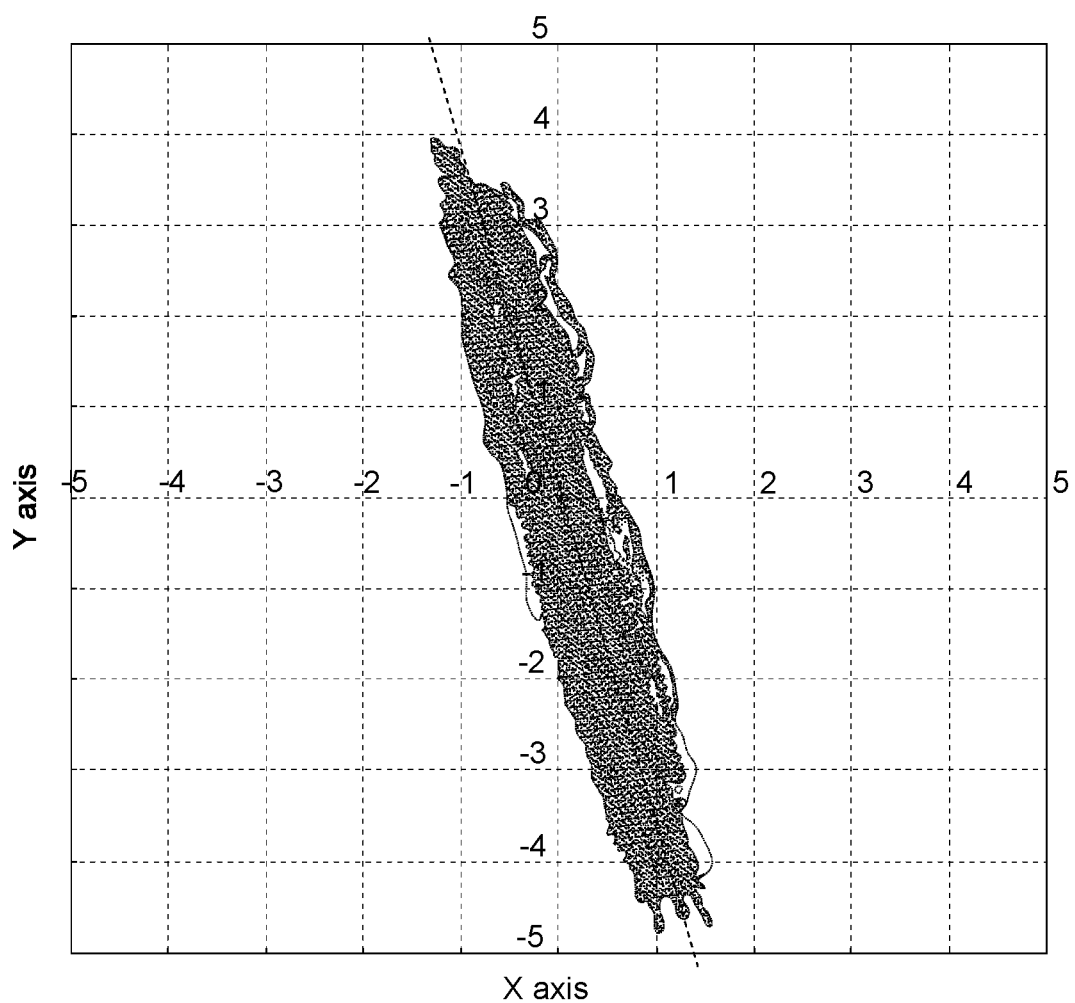
Figure 5:
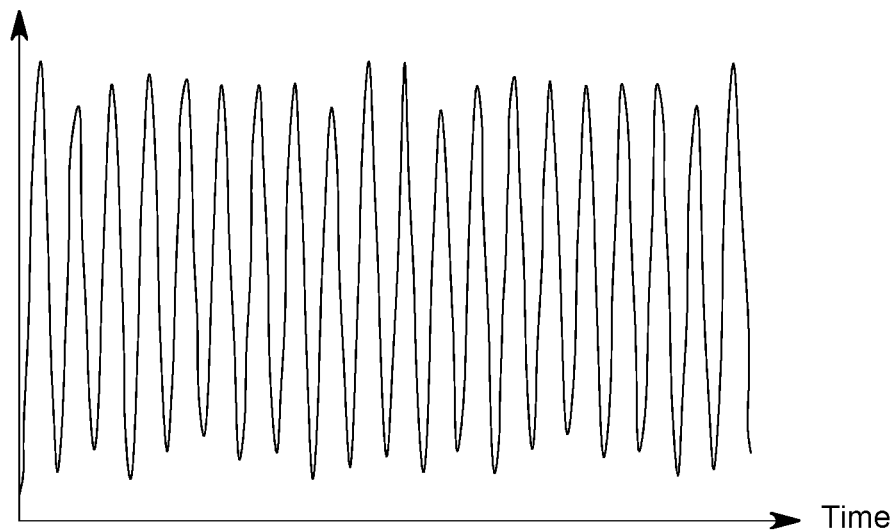
Figure 6:
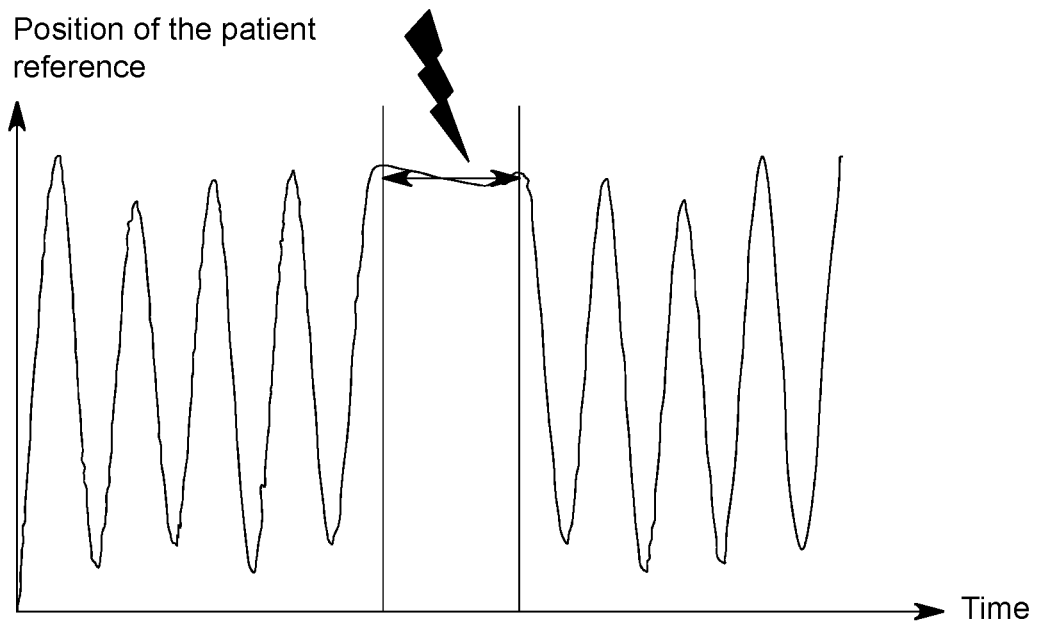
Figure 7:
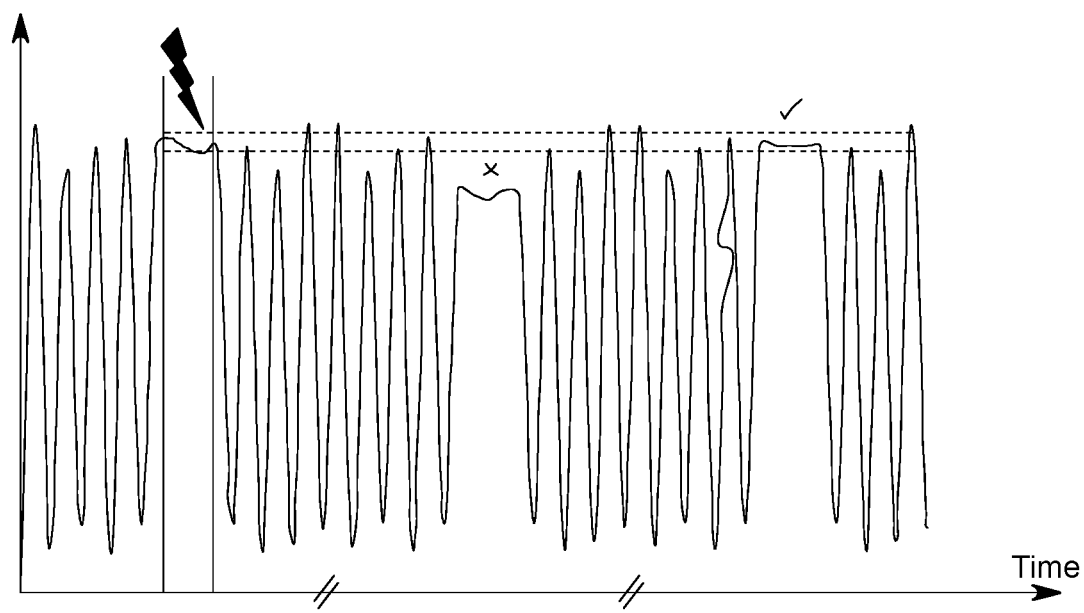

The features and advantages of the invention will emerge more clearly in light of the embodiments below, which are provided purely by way of illustration and in no way limit the invention, and with reference to FIGS. 1 to 7, in which:

FIG. 1 shows a schematic representation of a synchronization device according to the invention and of a medical robot, FIG. 2 shows an illustrative embodiment of a patient reference, FIG. 3 shows another illustrative embodiment of a patient reference of the synchronization device, FIG. 4 shows a recording, by a camera, of the movements, over time, of a patient reference positioned on the patient, FIG. 5 shows a curve illustrating the movements, over time, of a patient reference positioned on the patient, FIG. 6 shows a curve illustrating the movements, over time, of a patient reference positioned on the patient, during the acquisition of a medical image, FIG. 7 shows a curve illustrating the different steps of the method according to the invention.

DETAILED DESCRIPTION OF AN EMBODIMENT OF THE INVENTION

The invention relates to a method for determining an instant in the respiratory cycle of a patient in order to assist a medical intervention, in particular to guide an operator in performing a medical procedure. The medical intervention is of the minimally invasive type for example, in a target anatomical zone of a patient's body.

An illustrative embodiment of a device capable of implementing the method according to the invention is first described and illustrated schematically in FIG. 1. FIG. 1 also shows the patient 1 lying on an operating table 2.

The synchronization device is preferably adapted to be associated with an X-ray imaging device 40, as is illustrated in FIG. 1.

In a known manner, the X-ray imaging device 40 is configured to acquire a medical image of the patient in which, in particular, the target anatomical zone to be treated is visible. This medical image also makes it possible to plan the procedure of the operator or of a medical robot assisting the operator in a medical intervention. It can be used to determine the position that a medical instrument should take with respect to the target anatomical zone.

The synchronization device according to the invention can advantageously operate with any type of medical X-ray imaging device 40.

In non-limiting examples of X-ray imaging devices 40, mention may be made in particular of the CT scanner, or the CBCT imager (acronym for "Cone Beam Computed Tomography").

Also preferably, the synchronization device is adapted to be associated with a medical robot 50, as is illustrated in FIG. 1. The medical robot 50 is configured to assist a procedure performed by the operator during the medical intervention. Such a medical robot makes it possible, among other things, to help the practitioner to position, maintain or guide a medical instrument. An example of a medical robot will be described later, by way of illustration only.

The synchronization device comprises:
an element, hereinafter called a patient reference 10, intended to be positioned on the patient 1,
a locating device 20,
a control unit 30 configured to receive and process the data coming from the locating device 20 and those coming from the patient reference 10.

The control unit 30 is also configured to receive, via a wired or wireless means of communication, the medical image acquired by the X-ray imaging device 40 and to store said image.

The patient reference 10 is intended to be positioned on the body of the patient 1, close to the target anatomical zone of the patient. The patient reference 10 is positioned on the patient's body such that its movements follow the respiratory movements of the patient.

The patient reference 10 is configured, on the one hand, to be visible by the locating device 20 and, on the other hand, to be detectable in a medical image of the patient acquired by the X-ray imaging device 40.

The patient reference 10 advantageously has radiopaque markers 11, as is illustrated in FIGS. 2 and 3, which are configured to be detectable in the medical image. Preferably, the radiopaque markers 11 are at least three in number. The geometry and the respective positions of said radiopaque markers 11 are known in order to be able to precisely determine the position of the patient reference 10 with respect to the target anatomical zone on the medical image.

In preferred illustrative embodiments of radiopaque markers 11, said radiopaque markers 11 are radiopaque ceramic balls or radiopaque metal balls.

The patient reference 10 additionally has at least one locating element 12, as is illustrated in FIGS. 2 and 3, which is configured to be visible by the locating device 20. The at least one locating element 12 cooperates with the locating device 20.

The type of the at least one locating element 12 on the patient reference 10 depends on the locating device 20 used. The at least one locating element 12 will be described more precisely hereinbelow, in relation to the associated locating device 20.

The patient reference 10 additionally has an X-ray detector 13, as is illustrated in FIGS. 2 and 3. The X-ray detector 13 is intended to cooperate with the X-ray imaging device 40. The X-ray detector 13 is configured to detect when the X-ray emission has taken place, that is to say when the medical image has been taken.

In an illustrative embodiment, as shown in FIG. 2, the X-ray detector 13 is a dosimeter. Dosimeter signifies a sensor capable of measuring an irradiation dose. The dosimeter makes it possible in particular to detect the presence or absence of X-rays. The dosimeter can also indicate the dose of X-rays received over time. In an illustrative embodiment, the dosimeter is of the PIN photodiode type made of silicon and sensitive to X-rays. The dosimeter is configured to transmit to the control unit 30, via a wired communication means, data relating to the presence or absence of X-rays and the dose of X-rays received over time.

In another illustrative embodiment, as is illustrated in FIG. 3, the X-ray detector 13 is a scintillator. A scintillator is understood to mean a material which absorbs the X-rays emitted by the X-ray imaging device 40, and which emits a light signal that can be detected by a camera. In one example of a scintillator, the scintillator is an inorganic scintillator of the CsI (TI) type (cesium iodide doped with thallium). The camera is configured to transmit data, relating to the presence or absence of X-rays over time, to the control unit 30.

The control unit 30 receives and stores the data transmitted by the X-ray detector.

The locating device 20 is configured to acquire data relating to the position in time of the patient reference 10, within a reference frame of said locating device.

The movements of the patient reference 10, due to the breathing movements of the patient 1, are tracked and recorded by the locating device 20 by virtue of at least one locating element 12 positioned on said patient reference.

In one embodiment, the locating device is an optical locating device, preferably a camera 20.

In non-limiting examples, the camera can be:
an infrared stereoscopic camera,
a structured light camera,
a time-of-flight camera (or "ToF camera"),
a depth measurement camera (for example an RGB-D camera), etc.

The camera 20 is preferably coupled to at least three optical locating elements positioned on the patient reference 10.

In one embodiment, the optical locating elements are passive markers, for example reflecting spheres.

In another embodiment, the optical locating elements are active markers, for example elements emitting infrared light.

In one illustrative embodiment, when the camera 20 is an infrared stereoscopic camera, the optical locating elements 12 are reflecting spheres.

The optical locating elements are of known dimensions and are placed on the patient reference 10 according to a known geometry.

When a medical robot 50 is used to assist the operator during a medical intervention, optical locating elements, preferably of the same type as those positioned on the patient reference, are positioned on the medical robot.

The camera 20 is arranged in such a way that the optical locating elements 12 of the patient reference 10, and where appropriate those of the medical robot, are situated in a measurement zone of said camera.

The camera 20 is configured to carry out continuous image acquisitions, said images containing information on the coordinates of the optical locating elements 12, hence the coordinates of the patient reference and, where appropriate, those of the medical robot. The coordinates of the patient reference are transmitted continuously to the control unit 30 in order to be processed there and in order to determine the positions of the patient reference over time, and where appropriate those of the robot.

The optical locating elements 12 and the optical locating device form an optical navigation system.

In another embodiment, the locating device is an electromagnetic locating device, which has an electromagnetic field generator.

The electromagnetic field generator is preferably coupled to at least one electromagnetic locating element 12, called an electromagnetic sensor, which is positioned on the patient reference 10.

The at least one electromagnetic sensor has, for example, at least two conductive coils which can be configured to measure six degrees of freedom when said at least one electromagnetic sensor is subjected to an external electromagnetic field. Each coil of the at least one electromagnetic sensor produces an induced electrical signal having characteristics that depend on the position and orientation of the coil with respect to the electromagnetic field.

The coils of the at least one electromagnetic sensor are placed on the patient reference 10 according to a known geometry.

The electromagnetic field generator is arranged in such a way that the at least one electromagnetic sensor of the patient reference 10 is situated in a measurement zone of said electromagnetic field generator.

The electromagnetic field generator and the at least one electromagnetic sensor 12 make it possible to continuously acquire data on the position of the at least one electromagnetic sensor 12 of the patient reference.

The data acquired by the at least one electromagnetic sensor 12 are transmitted to the control unit 30 in order to be processed there and in order to determine the position of the patient reference 10.

One or more electromagnetic sensors can also be positioned on the medical robot, when it is envisioned to use such a medical robot for the medical intervention. These one or more electromagnetic sensors are preferably of the same type as those positioned on the patient reference 10. The data acquired by the one or more electromagnetic sensors are likewise transmitted to the control unit 30 in order to be processed there and in order to determine the position of the medical robot.

The one or more electromagnetic sensors and the electromagnetic locating device form an electromagnetic navigation system.

When the electromagnetic locating device is chosen, no camera is needed. It is thus preferable to use a dosimeter, rather than a scintillator (which requires a camera), as X-ray detector.

The control unit 30 simultaneously receives and records the data transmitted by the locating device, and those of the patient reference, and also the data, transmitted by the X-ray detector, relating to the dose of X-rays received by the patient reference over time or to the presence/absence of X-rays. The control unit 30 is configured to determine the positions of the patient reference 10, in particular during the acquisition of the medical image (in the case where the patient's breathing is blocked and in the case where the patient's breathing is not blocked), as will be described later.

The control unit 30 preferably has a memory module 31 in which the medical image and the various positions of the patient reference over time are recorded in particular.

The synchronization device preferably has a human-machine interface appliance 32. In one illustrative embodiment, the human-machine interface appliance is a display screen, preferably a touch screen.

The human-machine interface appliance 32 can be used to display the medical image or the evolution, over time, of the position of the patient reference 10.

The synchronization device can have an indicator light, for example a light emitting diode (LED). Said indicator light can be positioned near the human-machine interface appliance. The indicator light of the synchronization device is advantageously configured to transmit visual information (or a visual signal) to the operator at the time of the medical intervention.

The synchronization device can have an alarm. Said alarm is advantageously configured to transmit acoustic information (or an acoustic signal) to the operator at the time of the medical intervention.

As has been described above, the synchronization device can also be associated with a medical robot.

FIG. 1 illustrates an example of a medical robot. The medical robot has a base. The base of the medical robot can be equipped with wheels. As is illustrated in FIG. 1, this allows the medical robot to move in different directions by translational and/or rotational movements. The medical robot has an articulated arm 51, one end of which is connected to the base. A medical instrument can be mounted on a tool holder at the free end, called the distal end, of the articulated arm 51. The articulated arm 51 preferably has at least six degrees of freedom in order to be able to position and/or move the medical instrument in a three-dimensional space. The articulated arm can, for example, have one or more articulations.

The articulated arm 51 is controlled by a control unit of the medical robot.

In one embodiment, the control unit 30 of the synchronization device and the control unit of the medical robot are separate but linked to each other.

In another embodiment, as is illustrated in FIG. 1, the control unit 30 of the synchronization device and the control unit of the medical robot form one and the same control unit.

The medical robot 50 can have a human-machine interface appliance in order to allow the operator to control the robotic device and, optionally, to view images in relation to the medical procedure that is to be performed.

In a preferred embodiment, the human-machine interface appliance 32 of the synchronization device and the human-machine interface appliance of the medical robot form one and the same human-machine interface appliance.

The medical robot can also have an indicator light, for example a light emitting diode (LED). Said indicator light can be positioned on the articulated arm, for example at the distal end thereof. Said indicator light of the medical robot is configured to transmit visual information to the operator at the time of the medical intervention.

In a preferred embodiment, the indicator light of the synchronization device and the indicator light of the medical robot form one and the same indicator light.

The medical robot can also have an alarm. Said alarm is advantageously configured to transmit acoustic information (or an acoustic signal) to the operator at the time of the medical intervention.

In a preferred embodiment, the alarm of the synchronization device and the alarm of the medical robot form one and the same alarm.

The synchronization device and the medical robot form an assembly. The assembly can also include the X-ray imaging device 40.

The method for determining an instant of the respiratory cycle of the patient, in order to assist a medical intervention according to the invention, is now described. The purpose of such a method is to inform an operator, during a medical intervention, of the optimal time to perform the medical procedure, such as the insertion of a medical instrument into the body of the patient 1.

It is clear that the medical procedure as such, for example the insertion of the needle into the target anatomical zone of the patient 1, is performed by the operator only subsequent to the method according to the invention. The performance of such a medical procedure is therefore not part of the method according to the invention.

On the day planned for the intervention, before the method is carried out, the patient reference 10 is positioned on the patient's body, at the level of the target anatomical zone of the patient 1 that is to be treated. The patient is then placed, or has previously been placed, on the operating table. The movements of the patient reference 10 are considered to correspond to the respiratory cycle of the patient.

The method will be described in the case of an optical locating device, specifically a camera. The camera 20 is considered to be installed relative to the patient in such a way that the patient reference 10 is situated within the measurement zone of the camera.

Finally, in the case where the operator uses a medical robot for assistance, it is considered that the medical robot is placed close to the patient, at a position allowing the articulated arm of said medical robot to effect all the actions that are to be performed on the target anatomical zone of the patient.

In a first step 100, the movements of the patient reference 10 are recorded continuously.

The movements of the patient reference are visualized by the camera.

In an illustrative embodiment, the camera 20 continuously acquires images of its measurement zone and determines, for each image, the coordinates of the patient reference, using the optical locating elements 12 placed on the patient reference 10.

The camera continuously transmits the coordinates of the patient reference to the control unit 30 for processing and recording them in its memory module 31.

The camera preferably acquires the images at least throughout the duration of the method according to the invention.

The coordinates of the patient reference in each image correspond to the position of the patient reference within the reference frame of the camera.

In a second step 101, a medical image, namely an intra-operative image, of the target anatomical zone of the patient is obtained.

In a first embodiment, the patient's breathing has been blocked while the medical image is obtained.

In a first phase of this first mode, the patient's breathing is blocked.

In an illustrative embodiment of this first phase, when the patient is under general anesthesia, the ventilator of an anesthesia device is temporarily disconnected, for example at the end of inspiration or at the end of expiration. The patient is placed in so-called controlled apnea.

In another illustrative embodiment of this first phase, when the patient is under local anesthesia, the patient is asked to go into voluntary apnea, for example at the end of inspiration or at the end of expiration.

In a second phase of this first mode, an intra-operative medical image of the patient is acquired.

The intra-operative medical image is taken by means of the X-ray imaging device 40. The X-ray imaging device 40, for example a CT scan, is activated and emits X-rays in the direction of the patient, in particular the target anatomical zone.

The intra-operative medical image from the X-ray imaging device is transmitted to and stored in the memory module 31 of the control unit 30 of the synchronization device. The intra-operative medical image is also displayed on the human-machine interface appliance 32.

On this intra-operative medical image, it is possible to distinguish the patient reference 10, via the detection of the radiopaque markers 11, and the target anatomical zone.

During the emission of the X-rays by the X-ray imaging device 40, when the patient reference 10 of the synchronization device comprises a scintillator, said X-rays emitted by said X-ray imaging device 40 are absorbed by said scintillator. In response to this absorption, the scintillator emits a light signal detected by the camera.

The data relating to the absence or presence of X-rays are transmitted by the camera 20 to the control unit 30.

In a variant embodiment, during the emission of the X-rays by the X-ray imaging device 40, when the patient reference 10 of the synchronization device comprises a dosimeter, the X-rays emitted by said X-ray imaging device 40 are absorbed by said dosimeter. In response to this absorption, the dosimeter records the dose of X-rays that it absorbs.

The data relating to the dose of X-rays received per unit of time by the dosimeter are transmitted by the dosimeter to the control unit 30.

In a third phase of this first embodiment, after acquisition of the intra-operative medical image, the patient's breathing is unblocked.

In an illustrative embodiment of this third phase, when the patient is under general anesthesia, the ventilator is reconnected.

In another illustrative embodiment of this third phase, when the patient is under local anesthesia, the patient is asked to start breathing again.

In a second embodiment, the patient's breathing has not been blocked during acquisition of the medical image.

In this case, the acquisition of the image is carried out in a manner equivalent to that of the second phase of the first embodiment. The patient breathes normally during the acquisition of the medical image.

In a third step 102 of the method, a target position of the patient reference 10 during the acquisition of the intra-operative medical image is determined.

The control unit 30 continuously receives the coordinates of the patient reference in the reference frame of the camera and can deduce therefrom the positions, over time, of the patient reference, and therefore the respiratory cycle of the patient.

The coordinates of the patient reference 10, therefore its position, are obtained in the reference frame of the camera. However, the patient reference, depending on its orientation with respect to the ground, does not always follow a vertical movement perpendicular to the ground. Moreover, the camera may have been oriented such that its X axis is not always perpendicular to the ground. The movement of the patient reference can then be represented by a component on each of the axes of the camera.

FIG. 4 illustrates an example of an actual recording, taken for one minute by a camera, of the movements of a patient reference on a patient. Each point corresponds to a position, over time, of the patient reference, in an XY plane. In this example, it will be seen that the movement of the patient reference takes place along the axis drawn in dotted lines in FIG. 4.

For a better interpretation of the movement of the patient reference, and by analogy of the respiratory cycle of the patient, it is preferable to obtain a one-dimensional curve, illustrating the oscillatory movement of the patient reference, and therefore of the respiratory cycle of the patient, over time. There are different methods for obtaining this one-dimensional curve. Such methods are considered to be known to a person skilled in the art.

Mention may be made in particular of the method which consists in considering that the movement of the patient reference is vertical and in considering only the X axis of the camera, even if it is not perpendicular to the ground. However, in this case, part of the range of movement of the patient reference will be lost.

Mention may also be made of the more precise method which consists in carrying out a main-component analysis of the positions of the patient reference. These positions are analyzed with respect to the main axis of movement, called the main component (shown in dotted lines in FIG. 4 for example), which corresponds to the axis on which the respiratory movement takes place. The positions of the patient reference are displayed according to this main component. Such a method makes it possible to avoid possible movements of the camera that may generate a modification of the coordinates of the patient reference, even when the patient's respiratory movement is identical.

The curve in a continuous line in FIG. 5 shows an example of a representation of the movements of the patient reference, hence a representation of the respiratory cycle of the patient, over time.

This curve can be displayed on the human-machine interface appliance 32. Simultaneously, the control unit, on the other hand, continuously receives information from the X-ray detector 13.

When the patient reference 10 comprises a scintillator, the control unit receives, also from the camera, data relating to the presence or absence of X-rays. The control unit 30 determines those positions of the patient reference for which X-rays have been detected, and stores these positions in its memory module 31.

When the patient reference 10 comprises a dosimeter, the control unit receives, from said dosimeter via the wired communication means, data relating to the X-ray dose that it has received. The control unit 30 determines those positions of the patient reference for which the X-ray dose is greater than 0, strictly, and stores these positions in its memory module 31.

The positions stored in the memory module 31 correspond to the positions during the period of the exposure to X-rays, that is to say during the acquisition of the medical image.

During the period of the exposure to X-rays, whether in the case where the patient's breathing is blocked or in the case where the patient's breathing is not blocked, several positions of the patient reference are generally detected. These positions are not necessarily identical but are very close to each other, as is illustrated in FIG. 6. These positions are all the closer to each other as the patient's breathing is blocked.

To obtain a target position of the patient reference during the acquisition of the medical image, one solution consists in taking an average of said positions that are determined during the period of the exposure to X-rays. This solution advantageously makes it possible to avoid measurement noise of the camera.

Another solution, applicable only when the patient reference comprises a dosimeter, would consist in taking an average of said positions that are determined during the period of the exposure to X-rays, weighted by the X-ray dose received at each position.

Another solution would consist in calculating a median of said positions that are determined during the period of the exposure to X-rays. This solution advantageously makes it possible to overcome an aberrant position.

On the basis of the a priori knowledge of the dose curve received over time by a point object during the acquisition of medical images, another solution would consist in determining the position or positions of the patient reference during a specific phase of the exposure. This solution makes it possible to select with precision the positions of the patient reference during the phases of the exposure making the greatest contribution to the formation of the medical images.

At the end of this third step 102, the target position of the patient reference 10 during the acquisition of the intra-operative medical image is determined.

The movement of the patient reference 10 being equivalent to the movement of the respiratory cycle of the patient, the target position of the patient reference 10 corresponds to what is called a target phase of the respiratory cycle over time.

The operator can now plan the medical intervention, for example the insertion of a needle into the body of the patient, from a medical image.

In one embodiment, the operator himself performs the medical insertion procedure.

In another embodiment, the operator is assisted by the medical robot 50, and the medical procedure is performed by said medical robot. The medical robot 50 is then configured according to an intervention plan that will be stored in the memory module 31 of the control unit 30. The medical robot positions itself, with respect to the patient, in accordance with the intervention plan and by virtue of the optical navigation system.

The intervention plan is generated from a medical image.

In an illustrative embodiment, the intervention plan is generated from the intra-operative medical image acquired by the X-ray imaging device 40 during the second step 101 of the method.

In another illustrative embodiment, the intervention plan is generated from what is called a pre-operative medical image. This pre-operative medical image has been taken before the medical intervention, for example several days or several hours before the medical intervention. In this case, the actual position of the anatomy of interest of the patient at the time of the intervention does not necessarily correspond to a position that has been predicted or modeled during a pre-operative planning phase. It is therefore advantageous to be able to realign a pre-operative image, from which an action to be performed on the target anatomical zone is planned, with an intra-operative image precisely showing the position of the target anatomical zone of the patient 1 at the time of the intervention.

There are different methods of realigning one image with another. Such methods are considered to be known to a person skilled in the art.

In a fourth step 103, a candidate position of the patient reference 10 is determined.

In a first embodiment of this fourth step, the determination of the candidate position is carried out during a temporary blocking of the patient's breathing.

In a first phase of this first embodiment, the patient's breathing is again blocked. Breathing should preferably be blocked at the same phase of the respiratory cycle as during the acquisition of the medical image.

In an illustrative embodiment of this first phase, in order to decide when to block the patient's breathing, when the patient is under general anesthesia for example, the operator can rely for example on the position of the bellows of the ventilator of the anesthesia system, by positioning the bellows substantially at the same position as the position of the bellows when breathing was blocked for the acquisition of the medical image.

In another illustrative embodiment of this first phase, it is possible to use a predictive model of the respiratory cycle of the patient. From the recording of the movements of the patient reference over time, and therefore of the patient's respiratory movement, it is possible to estimate a predictive model of the respiratory cycle. This predictive model is determined by the control unit 30.

FIG. 5 illustrates, in broken lines, the predicted positions, over time, of the patient reference, and therefore the predicted respiratory cycle of the patient.

From this prediction, it is then possible to anticipate the instant when the patient's breathing should be blocked.

The control unit 30 can transmit information to the operator, for example in the form of an acoustic or visual signal, indicating that he can block the patient's breathing.

In a second phase of the first embodiment, after the patient's breathing is blocked, the candidate position of the patient reference 10 is determined.

This candidate position is determined from the coordinates of the patient reference that are acquired by the camera, as explained during the third step 102 of the method.

In a second embodiment of the fourth step, the determination of the candidate position is carried out without blocking, even temporarily, the patient's breathing.

In an illustrative embodiment of this second mode, it is possible to use a predictive model of the respiratory cycle of the patient. From the recording of the movements of the patient reference over time, and therefore of the patient's respiratory movement, it is possible to estimate a predictive model of the respiratory cycle. This predictive model is determined by the control unit 30.

From this prediction, it is then possible to anticipate the instant when the patient reference is close to the target position.

The candidate position of the patient reference 10 is then determined. This candidate position is determined from the coordinates of the patient reference that are acquired by the camera, as explained during the third step 102 of the method.

In a fifth step 104, the candidate position of the patient reference 10 is compared to the target position.

The comparison of the candidate position with the target position, stored in the memory module 31, is carried out by the control unit.

Case where the Candidate Position is Determined During the Blocking of the Patient's Breathing (First Embodiment of the Fourth Step)

When the candidate position of the patient reference 10 is within a predefined tolerance range with respect to the target position, it is considered that the patient's breathing has been blocked at an opportune moment, that is to say at the same phase of the respiratory cycle as during the acquisition of the medical image. The tolerance range is preferably ±10% of the target position, more preferably ±5% of the target position. Information is then transmitted in order to signal that the intervention can begin, that is to say that the time is optimal for performing the medical procedure, for example the insertion of a medical instrument toward the target anatomical zone of the patient.

In one illustrative embodiment, the information is transmitted to the operator.

This information can be transmitted for example in the form of an acoustic signal via the indicator light of the synchronization device, and/or a visual signal via the alarm of the synchronization device, on the human-machine interface appliance 32 and/or via an indicator light of the LED type, for example that of the medical robot, when the operator is assisted by said medical robot. The indicator light of the synchronization device and/or of the medical robot can for example emit a light of fixed color.

In another illustrative embodiment, when the operator is assisted by the medical robot 50, the information is transmitted directly to the medical robot. The medical procedure is automatically triggered and performed by the medical robot. When the medical intervention is completed, the patient's breathing is unblocked.

When the candidate position of the patient reference 10 is not within the predefined tolerance range with respect to the target position, it is considered that the patient's breathing has not been blocked at the same phase of the respiratory cycle as during the acquisition of the medical image. Information is then transmitted to the operator to signal to him not to start the operation, that is to say that the time is not optimal for performing the medical procedure. This information can be transmitted for example in the form of an acoustic signal via the alarm of the synchronization device, or a visual signal via the indicator light of the synchronization device, on the human-machine interface appliance 32 or via the indicator light, of the LED type, for example that of the medical robot, when the operator is assisted by said medical robot. The indicator light of the synchronization device and/or of the medical robot can for example emit a flashing color light.

The patient's breathing is then unblocked.

Steps 103 and 104 are repeated until the candidate position of the patient reference 10 is within a predefined tolerance range with respect to the target position.

When the medical intervention is completed, the patient's breathing is unblocked.

Case where the Candidate Position is Determined without Blocking the Patient's Breathing (Second Embodiment of the Fourth Step)

When the candidate position of the patient reference 10 is within a predefined tolerance range with respect to the target position, it is considered that the phase of the respiratory cycle of the patient is close to the same phase of the respiratory cycle as during the acquisition of the medical image. The tolerance range is, for example, between ±10% of the target position, preferably between ±5% of the target position, or more preferably between −10% and −5% of the target position. Information is then transmitted to signal that the intervention can begin, that is to say that the time is optimal for performing the medical procedure, for example the insertion of a medical instrument toward the target anatomical zone of the patient.

In one illustrative embodiment, the information is transmitted to the operator. This information can be transmitted for example in the form of an acoustic signal via the indicator light of the synchronization device, and/or a visual signal via the alarm of the synchronization device, on the human-machine interface appliance 32 and/or via an indicator light, of the LED type, for example that of the medical robot, when the operator is assisted by said medical robot. The indicator light of the synchronization device and/or of the medical robot can for example emit a light of fixed color.

In another illustrative embodiment, when the operator is assisted by the medical robot 50, the information is transmitted directly to the medical robot. The medical procedure is automatically triggered and performed by the medical robot.

When the candidate position of the patient reference 10 is not within the predefined tolerance range with respect to the target position, it is considered that the phase of the respiratory cycle of the patient is close to, and upstream of, the same phase of the respiratory cycle as during the acquisition of the medical image. Information is then transmitted to the operator to signal to him not to start the operation, that is to say that the time is not optimal for performing the medical procedure. This information can be transmitted for example in the form of an acoustic signal via the alarm of the synchronization device, or a visual signal via the indicator light of the synchronization device, on the human-machine interface appliance 32 or via the indicator light, of the LED type, for example that of the medical robot, when the operator is assisted by said medical robot. The indicator light of the synchronization device and/or of the medical robot can for example emit a flashing color light.

Steps 103 and 104 are repeated until the candidate position of the patient reference 10 is within a predefined tolerance range with respect to the target position, still without blocking the breathing.

The embodiments of the method and of the synchronization device that have been considered above have been described by way of non-limiting examples, and other variants can therefore be envisioned.

In particular, the method has been described in the case of an optical locating device, specifically a camera. The method can be applied, by analogy, to the electromagnetic locating device, without departing from the scope of the invention.

The above description clearly illustrates that, by virtue of its various features and their advantages, the present invention achieves the objectives set. In particular, the method makes it possible to detect the exact instant of the respiratory cycle of the patient during the acquisition of the medical image and to determine the optimal moment of the respiratory cycle for assisting the operator in performing the medical procedure.

The invention claimed is:

1. A synchronization device for determining an instant of a respiratory cycle of a patient in order to assist a medical intervention on said patient, said device comprising:
   a locating device,
   a reference device which comprises radiopaque markers, configured to be positioned on a body of the patient,
   at least one locating element configured to be detectable by the locating device, wherein the at least one locating element including a marker,
   an X-ray imaging device, and
   an X-ray detector configured to cooperate with the X-ray imaging device,
   a memory; and
   a processor, the processor coupled to the memory and configured to:
   record and process data obtained from the locating device and the reference device,
   wherein the locating device is configured to continuously record movements of the reference device, the movements of the reference device corresponding to a respiratory cycle of the patient, and to transmit to the processor data relating to the movements of the reference device, in that the X-ray detector is configured to detect when a medical image has been taken by the X-ray imaging device and to transmit the corresponding data to the processor, and,
   determine a target position of the reference device in the medical image, acquired at a time when the respiratory cycle has been blocked, from the at least one locating element, positioned on the reference device, and from the X-ray detector,
   determine a candidate position of the reference device from the at least one locating element positioned on the reference device, at a time when the respiratory cycle has again been blocked,
   compare the candidate position and the target position,
   when the candidate position is not within a predefined tolerance range with respect to the target position, repeating determine the candidate position and compare the target and candidate positions until the candidate position is within a predefined tolerance range with respect to the target position, and
   estimate, from a predictive model of the respiratory cycle of the patient, a moment of blocking of breathing of the patient during the determination of the candidate position.

2. The synchronization device of claim 1, wherein the locating device is an optical locating device, and the reference device further comprise at least three optical locating elements.

3. The synchronization device of claim 1, wherein the locating device is an electromagnetic locating device, and the reference device further comprise at least one electromagnetic locating element.

4. The synchronization device of claim 1, wherein the X-ray detector is a dosimeter or a scintillator.

5. The synchronization device of claim 1, wherein the processor is further configured to determine, from all the positions taken by the reference device during a period of an exposure to X-rays, the target position of the reference device.

6. The synchronization device of claim 1, further comprising a human-machine interface appliance configured to inform an operator, using an acoustic signal and/or a visual signal, of a result of a comparison between the candidate position and the target position.

7. The synchronization device of claim 1, wherein the processor is further configured to plan an intervention, assisted by a medical robot, at a time between determining the target position and the candidate position.

8. An assembly comprising a medical robot and the synchronization device of claim 1, the medical robot comprising a base, an articulated arm, one end of the robotic arm is connected to the base, and a control unit.

9. The synchronization device of claim 1, wherein the respiratory cycle has been blocked based on administration of general anesthesia, and a ventilator of an anesthesia device is temporarily disconnected.

10. The synchronization device of claim 1, wherein the respiratory cycle has been blocked based on administration of local anesthesia, and the patient directed to go into a voluntary apnea.

11. The synchronization device of claim 6, wherein the human-machine interface appliance is a display screen.

12. The assembly of claim 8, wherein the control unit of the medical robot and the control unit of the synchronization device form one control unit.

13. The assembly of claim 8, wherein the medical robot has a human-machine interface appliance.

14. A method for determining an instant of a respiratory cycle of a patient in order to assist a medical intervention on said patient, comprising steps of:
   continuous recording of movements of a reference device placed near a target anatomical zone of the patient, the movements of the reference device corresponding to the respiratory cycle of the patient,
   acquiring, by an X-ray imaging device, a medical image of said target anatomical zone of the patient,
   determining a target position of the reference device during the acquiring of the medical image, from at least one locating element, positioned on the reference device, and from an X-ray detector,
   determining a candidate position of the reference device, from the at least one locating element positioned on the reference device, and
   comparing the candidate position and the target position,
   wherein the instant when the candidate position is within a predefined tolerance range with respect to the target position is estimated from a predictive model of the respiratory cycle of the patient.

15. The method of claim 14, wherein the target position of the reference device is determined from all the positions taken by the reference device during a period of exposure to X-rays.

16. The method of claim 14, wherein an acoustic signal and/or a visual signal is generated when the candidate position is within a predefined tolerance range with respect to the target position.

17. The method of claim 14, further comprising a step of planning an intervention, assisted by a medical robot, between the steps of determining the target position and the candidate position.

18. An assembly for implementation of the method of claim 14 comprising:
   a medical robot comprising a base, an articulated arm, one end of the articulated arm is connected to the base, and a control unit;
   an X-ray imaging device, and
   a synchronization device comprising:
   a locating device, configured to continuously record movements of the reference device, the movements of the reference device corresponding to the respiratory cycle of the patient, and to transmit them to the control unit, a reference device, configured to be positioned on a body of the patient, and including radiopaque markers, at least one locating element configured to be detectable by the locating device, and an X-ray detector intended to cooperate with the X-ray imaging device, a processor for recording data from the locating device and the reference device, and configured to:

determine the positions of the reference device during acquisition of the medical image, during a period of exposure to X-rays, from the at least one locating element, positioned on the reference device, and from the X-ray detector, determine a target position of the reference device from all the positions of the reference device during the acquisition of the medical image, determine a candidate position of the reference device, from the at least one locating element positioned on the reference device, compare the candidate position and the target position, estimate, from a predictive model of the respiratory cycle of the patient, a moment of blocking of breathing of the patient during the determination of the candidate position.

19. The assembly of claim 18, wherein the control unit of the medical robot and the control unit of the synchronization device form one control unit.

* * * * *